United States Patent
Brehm

(10) Patent No.: US 6,460,601 B1
(45) Date of Patent: Oct. 8, 2002

(54) METHOD OF PRODUCING INTERNAL SCREW THREADS, ESPECIALLY IN METALS OR THEIR ALLOYS

(75) Inventor: Peter Brehm, Senden (DE)

(73) Assignee: Bredent Dentalgerate U. Materialien Fach- U. Organisationsberatung Peter Brehm, Senden (DE)

( * ) Notice: Subject to any disclaimer, the term of this patent is extended or adjusted under 35 U.S.C. 154(b) by 0 days.

(21) Appl. No.: 09/548,854

(22) Filed: Apr. 13, 2000

(51) Int. Cl.[7] .......................... B22D 29/00; A61C 13/00; A61C 13/20
(52) U.S. Cl. .......................... 164/132; 164/137; 249/59; 433/174
(58) Field of Search .......................... 164/132, 131, 164/35, 45, 98, 111, 345, 376, 137; 249/54, 59; 433/174

(56) References Cited

U.S. PATENT DOCUMENTS

| | | | |
|---|---|---|---|
| 3,112,540 A | * 12/1963 | Kaneko et al. | 164/111 |
| 3,945,070 A | * 3/1976 | Hauser | 470/18 |
| 4,079,475 A | * 3/1978 | Thompson | 470/26 |
| 4,172,867 A | * 10/1979 | Devault | 264/16 |
| 4,240,498 A | * 12/1980 | Frenette | 164/303 |
| 4,554,962 A | * 11/1985 | Wright | 164/132 |
| 4,682,644 A | * 7/1987 | Ueno | 164/359 |
| 4,840,219 A | * 6/1989 | Foreman | 164/369 |
| 4,917,347 A | * 4/1990 | Fenick | 249/54 |
| 4,958,676 A | * 9/1990 | Kuntz | 164/340 |
| 5,232,365 A | * 8/1993 | Ikehara | 433/213 |
| 5,518,679 A | * 5/1996 | Junk | 264/318 |
| 5,931,675 A | * 8/1999 | Callan | 433/173 |

* cited by examiner

*Primary Examiner*—M. Alexandra Elve
*Assistant Examiner*—Kevin P. Kerns
(74) *Attorney, Agent, or Firm*—Herbert Dubno

(57) ABSTRACT

A method of producing internal screw threads, especially in metals or their alloys and preferably in high strength alloys as are used, inter alia, in dental prosthetics, especially employing the casting technique. Initially an externally threaded pin is positioned in a mold cavity at the location in the dental prosthetic article required for the internal thread. The molten metal is cast around this metal pin and, after hardening of the molten metal, is removed to leave an internal screw thread.

2 Claims, 2 Drawing Sheets

METHOD OF PRODUCING INTERNAL SCREW THREADS, ESPECIALLY IN METALS OR THEIR ALLOYS

FIELD OF THE INVENTION

The present invention relates to a method of producing internal screw threads, especially in metals or their alloys and particularly in such high-strength alloys as are commonly used, inter alia, in dental prostheses and especially utilizing casting techniques for the production of such dental prostheses.

BACKGROUND OF THE INVENTION

In the formation of dental prostheses, for example crowns, plates and multiple-tooth sets it is common practice to utilize high strength metal alloys and to provide in such metal bodies, internal screw threads which serve for connection purposes and for fastening to the body. The formation of such internal screw threads in high strength metal bodies has, in the past, posed a problem.

On the one hand, because of the metal used, usually a high strength alloy like, for example, a chromium-cobalt alloy, the Vickers hardness can range up to 500. In such materials the cutting of screw threads, for example, to a depth of 2 mm as is generally required, is particularly difficult. On the one hand, threaded bores are often required in interior regions in dental prosthetics and it is frequently impossible to provide sufficient room for a thread-cutting tap in the regions where such internally threaded bores are required.

To overcome this problem, it is known to provide internally threaded sleeves which are mounted in the casting mold and are secured in the solid body by embedding the sleeves in the hardened melt. A drawback of this technique, however, is that the sleeves themselves require significant space which is not always available. In addition, the melting point of the sleeve must be higher than that of the metal in which the sleeve is embedded and that means that different metals may have to be used in the dental prosthesis which is, as a rule, undesirable.

OBJECTS OF THE INVENTION

It is the principal object of the present invention to provide an improved method of making internal threads in a cast metal body which is greatly simplified by comparison to earlier techniques and elements the problems hitherto encountered with conventional thread cutting methods.

Another object of the invention is to provide a method of making a dental prosthesis which obviates drawbacks of earlier techniques.

SUMMARY OF THE INVENTION

These objects are achieved, in accordance with the invention, by a method of forming an internal screw thread in a metal body which comprises the steps of:
(a) positioning an externally threaded pin in a casting mold at a location at which an internal screwthread is desired;
(b) filling the mold with a melt of the metal of the body whereby the melt surrounds the pin;
(c) hardening the metal in the mold to form the metal body and embed the pin therein; and
(d) thereafter removing the pin from the hardened metal of the body, thereby leaving an internal screwthread therein.

As applied to the making of a dental prosthesis the method can comprise the steps of:
(a) forming an externally threaded pin with a cylindrical shaft, an externally threaded portion at an end of the shaft, and a cylindrical projection of a diameter less than that of the externally threaded portion extending axially from the externally threaded portion;
(b) positioning the externally threaded pin in a casting mold having a configuration of a dental prosthesis at a location at which an internal screwthread is desired;
(c) filling the mold with a melt of a high-strength metal dental-prosthesis alloy whereby the melt surrounds the pin;
(d) hardening the metal in the mold to form a metal body of the dental prosthesis and embed the pin therein; and
(e) thereafter removing the pin from the hardened metal of the body, thereby leaving an internal screwthread therein.

The projection of the pin forms a cylindrical pocket aligned with the internally threaded bore for receiving a synthetic resin.

More particularly, the objects of the invention are achieved by providing at each location in the mold at which an internal thread is required, a respective pin formed with an outer thread and which projects into the mold cavity so that it is embedded in the hardened metallic melt, the threaded pin being subsequently removed from the hardened body.

With the invention, any machining of the high strength metal is obviated and none of the force required for thread cutting is applied to the dental prosthesis product. The threaded pin can be positioned with high precision before filling of the mold and without any expenditure of force.

According to a feature of the invention, the threaded pin can be composed of a ceramic or some similar material resistant to high temperatures, i.e. a refractory material.

In order to expose the internal screw thread so that it can be used for connection purposes, the threaded pin must be removed and this can be accomplished in a simple manner, just by unscrewing it from the body.

If this is not possible for some reason or another approach may be desired, the threaded pin can be removed after hardening of the metal melt by sandblasting or drilling it out.

Finally, it has been found to be advantageous to provide the threaded pin at one end with a cylindrical shaft from which the externally threaded portion extends while, at the opposite end of the externally threaded portion, a small diameter cylindrical projection is formed. The cylindrical projection can have a diameter less than that of the threaded portion. The cavity formed by the projection can serve to receive the synthetic resin material in a cartridge or body of the synthetic resin which lies ahead of the free end of any screw which is later threaded into the internally threaded bore.

The synthetic resin material forms a bonding agent which prevents loosening of the screw by increasing the friction with which it is held. The cylindrical shaft serves to hold the threaded pin in the refractory mass forming the mold.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
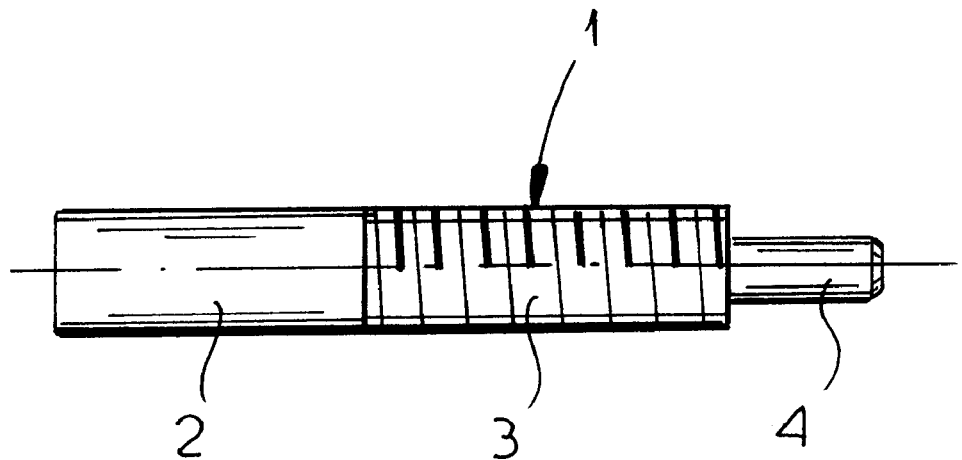
FIGS. 1 and 2 are diagrammatic elevational views of pins of two slightly different shapes in accordance with the invention.

The pins 1 shown in the drawing are externally threaded and serve, in the method of the invention, for producing an internal screw thread in a prosthesis. Primarily such threaded pins are used to produce internal screw threads in high strength alloys of the type used in dental prostheses and especially in the casting technique for producing dental prostheses such as crowns, bridges and the like.

The bridge or other dental prosthesis is provided with such internal screw threads to enable connections or fastenings of different kinds to be realized and without the need to machine or cut threads in the high strength material which is usually a chromium-cobalt alloy having a Vickers hardness of up to 500. Up to now, such threads were cut in the high strength alloy to a depth of about 2 mm.

Figure 3:
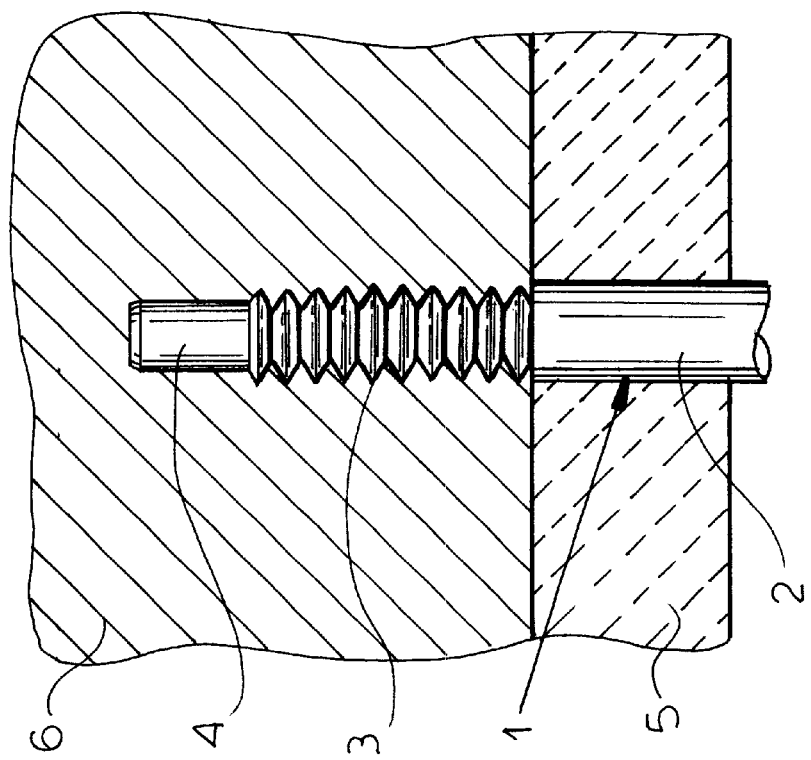
FIG. 3 is a cross sectional view through a mold showing the molten metal therein surrounding a pin according to the invention.

With the method of the invention, the pin 1 is inserted into a casting mold 5 (FIG. 3) so that its external screw thread 3 lies in the mold cavity.

The precisely positioning of the pin can be accomplished with ease since the cylindrical shaft 2 of the pin locates it with precision in the mold cavity.

Figure 4:
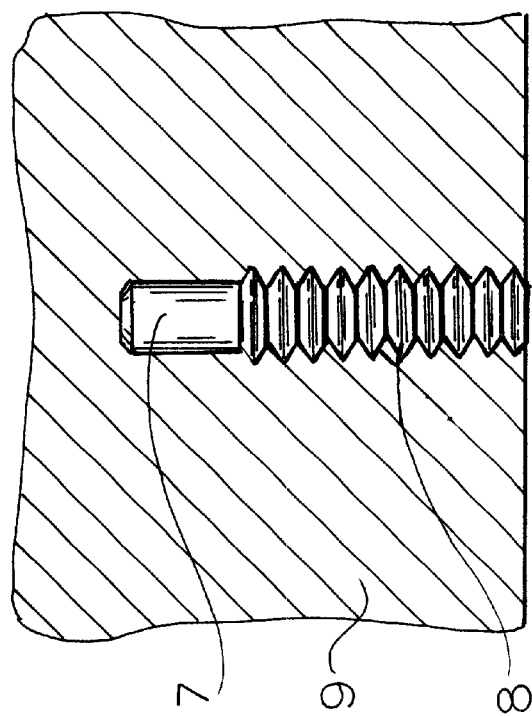
FIG. 4 shows the internally threaded portion of a dental prosthesis after removal of the externally threaded pin and before a synthetic resin is introduced into the cavity and a screw is inserted in the hole.

Molten metal 6 is cast into the mold and once that metal melt hardens the pin 1 is removed. As shown in FIG. 4, upon removal of the pin the hardened body 9 of the high strength dental prosthetic alloy 9 is left with the internal screw thread 8 and a cylindrical pocket 7 formed by the casting of the molten metal around the projection 4 of the pin.

The pin here provides a kind of lost-form member since it is ultimately removed and that, of course, insures a highly precise positioning of the internal thread without the need for significant force.

The pin 1 can be comprised of ceramic or another high temperature material, the material preferably being selected so that it has low adhesion to the cast metal mass and easily can be unscrewed.

As noted, it can also be removed by sandblasting.

Figure 2:
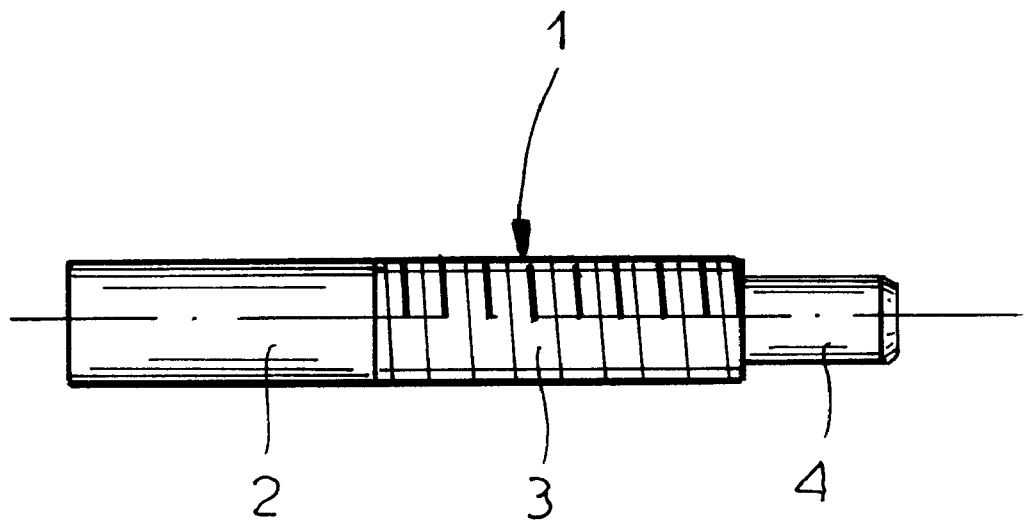

In FIGS. 1 and 2 the preferred configuration of the threaded pin 1 is shown and has at one end the cylindrical shaft 2 while at the other end of the threaded portion 3, a cylindrical projection 4 is formed with a diameter smaller than that of the threaded portion.

I claim:

1. A method of forming an internal screwthread in a metal body of a dental prosthesis, comprising the steps of:

(a) positioning an externally threaded one-piece pin composed of a refractory material in the form of a ceramic in a casting mold at a location at which an internal screwthread is desired or said pin being formed with a cylindrical shaft, an externally threaded portion at an end of said shaft, and a cylindrical projection of a diameter less than that of said externally threaded portion extending axially from said externally threaded portion;

(b) filling said mold with a melt of a high-strength metal dental prosthesis alloy and adapted to constitute upon hardening the metal of said body whereby said melt surrounds said externally threaded portion of said pin;

(c) hardening the metal in said mold to form said metal body and embed said pin therein; and (d) thereafter removing said pin from the hardened metal of said body, thereby leaving an internal screwthread therein.

2. A method of making a dental prosthesis, comprising the steps of:

(a) forming an externally threaded one-piece pin of a ceramic material with a cylindrical shaft, an externally threaded portion at an end of said shaft, and a cylindrical projection of a diameter less than that of said externally threaded portion extending axially from said externally threaded portion;

(b) positioning said externally threaded pin in a casting mold having a configuration of a dental prosthesis at a location at which an internal screwthread is desired;

(c) filling said mold with a melt of a high-strength metal dental-prosthesis alloy whereby said melt surrounds said externally threaded portion of said pin;

(d) hardening the metal in said mold to form a metal body of said dental prosthesis and embed said pin therein; and (e) thereafter removing said pin from the hardened metal of said body, thereby leaving an internal screwthread therein.

* * * * *